United States Patent [19]
Vezzani

[11] Patent Number: 5,635,122
[45] Date of Patent: Jun. 3, 1997

[54] PROCESS FOR DISPOSING OF REFUSE WHICH INCLUDES PATHOGENIC COMPONENTS

[75] Inventor: Corrado Vezzani, Milan, Italy

[73] Assignee: Vomm Impianti E Processi S.r.l., Milan, Italy

[21] Appl. No.: 328,251

[22] Filed: Oct. 24, 1994

[51] Int. Cl.⁶ .......................... A61L 11/00; B27N 1/00
[52] U.S. Cl. ................ 264/115; 241/17; 241/606; 241/DIG. 38; 422/26; 422/308
[58] Field of Search .................... 241/606, DIG. 38, 241/17; 264/109, 115; 422/11, 26, 295, 307, 308, 312; 588/258; 494/13

[56] References Cited

U.S. PATENT DOCUMENTS

| | | | |
|---|---|---|---|
| 3,547,577 | 12/1970 | Lovercheck | 241/DIG. 38 |
| 5,048,766 | 9/1991 | Gaylor et al. | 241/DIG. 38 |
| 5,119,994 | 6/1992 | Placzek | 422/26 |
| 5,213,774 | 5/1993 | Noetzel | 422/305 |
| 5,346,142 | 9/1994 | Miller et al. | 241/DIG. 38 |

FOREIGN PATENT DOCUMENTS

| | | |
|---|---|---|
| WO-A-9212738 | 8/1992 | WIPO. |

*Primary Examiner*—David A. Simmons
*Assistant Examiner*—Kenneth M. Jones
*Attorney, Agent, or Firm*—Rosen, Dainow & Jacobs, L.L.P.

[57] ABSTRACT

A process is described in which hospital refuse is comminuted to a powder-like consistency or at least so as to be capable of being pumped and subsequently subjected to heat sterilisation treatment in a highly turbulent dynamic thin layer.

17 Claims, 3 Drawing Sheets

PROCESS FOR DISPOSING OF REFUSE WHICH INCLUDES PATHOGENIC COMPONENTS

In its most general aspect the present invention relates to a method for disposing of refuse which includes pathogenic and/or toxic components.

More particularly this invention relates to a method for the sterilisation and disposal of hospital refuse.

It is well known that the disposal of hospital refuse currently constitutes a serious problem from an environmental point of view. In fact, because of its pathogenic germ content such refuse cannot be disposed of via the usual discharge means authorised for the so-called urban refuse.

On the other hand the extremely varied nature of the composition of such refuse makes its disposal by incinerator means equally problematic.

As well as artificial, synthetic or vegetable fibre material (such as gauzes or cloths), for example sheets of the so-called one-time use type, such refuse contains rubber, metal and plastics materials as well as disinfectant residues and residues of other medical substances widely utilised in hospitals.

These components (in particular the plastics and disinfectants) often contain fluorinated compounds which have a well known tendency to generate compounds of the tetrachlorodibenzodioxin type following treatments at high temperature, such as are utilised in incinerators.

The risk and the noxious nature of these latter compounds, commonly called dioxins, is well known and constitutes the main reason why the use of incinerators for the disposal of hospital refuse is not acceptable.

For the reasons explained above the necessity of finding a method of disposal of hospital refuse which overcomes the problems of the environmental impact caused by the use of incinerators is currently very strongly felt.

In order, on the one hand, to overcome the disadvantages related to the use of incineration installations and, on the other hand, to overcome the risk of allowing the survival of pathogenic germs which are always present in hospital refuse, methods have been proposed which provide for the sterilisation of the hospital refuse before being sent to the normal urban refuse discharge.

In one of these methods the sterilisation is effected by subjecting successive charges of refuse to respective heat treatments in rotating drums in a discontinuous manner.

This method has, however, the disadvantage of a high fire risk because of the presence of cellulosic fibres and solvents in the materials to be treated.

This fire risk is not even eliminated by working in the absence of oxygen in that the peroxide groups present in the rubbers as a consequence of the vulcanisation process can act to support combustion in place of atmospheric oxygen.

Moreover, in this batch process the individual charges of refuse have a significant mass such that the heat treatment is necessarily non-uniform and consequently the complete sterilisation throughout the whole mass of the material is not guaranteed.

To overcome the recognised disadvantages of the batch process (the treatment of successive loads of large mass) attempts have been made to sterilise hospital refuse by utilising a technology based on the use of microwaves; even in this case there are serious problems related to the safety of the installation.

Micrometric waves at high energy (microwaves) utilised in such installations can in fact be extremely dangerous, for example as a result of uncontrollable and unpredictable reflection phenomena due to the presence of, for example, metal objects in the refuse to be treated. Because they require very strict safety measures and highly specialised personnel such installations involve very high management costs and notwithstanding this do not always give satisfactory results.

The problem on which the present invention is based is that of making available a method for the disposal of hospital refuse which can satisfy current requirements as explained more fully above, whilst contemporaneously overcoming the disadvantages discussed with reference to the prior art.

The technical solution of this problem is to subject small quantities of hospital refuse maintained in a highly turbulent state and constituting a substantially continuous flow of material to a sterilising heat treatment.

According to this idea the technical problem is resolved according to the present invention by a method for disposal of hospital refuse and the like characterised by the fact that it comprises the steps of:

grinding hospital refuse to obtain a comminuted material which can be pumped;

sterilisation heat treatment of the comminuted material disposed in a thin layer and maintained in a highly turbulent condition cooling of the sterilised comminuted material and disposal thereof by discharge.

In accordance with a further characteristic of the invention, the sterilisation heat treatment is effected by making the comminuted material flow in a continuous thin and turbulent layer in contact with a heated wall.

Advantageously the method of this invention is put into practice by utilising sterilisation apparatus comprising a cylindrical tubular body provided with a heating jacket, an inlet opening for the material to be treated and a discharge opening for treated material, and a paddle rotor rotatably supported in the cylindrical body and driven to rotate at 200–1500 revolutions per minute.

Such apparatus will be identified hereafter in the description and in the subsequent claims with the term turbosteriliser.

By utilising such apparatus the method of disposing of hospital refuse according to the present invention comprises the steps of:

comminuting the hospital refuse to obtain a pumpable comminuted material, supply of a continuous flow of this material to the inlet of a turbosteriliser having cylindrical internal walls heated to a temperature of 300°–500° C. and in which the paddle rotor is rotated at a speed lying between 400 and 1500 revolutions per minute, centrifuging of the comminuted material to form a thin tubular layer which flows in contact with the heated wall towards the discharge aperture with contemporaneous sterilisation of the comminuted material, cooling and recovery of the sterilised and comminuted material and subsequently delivering it to a discharge outlet.

Contemporaneously with the heat sterilisation of the comminuted material maintained in a dynamic thin layer it is dried by the removal in the form of steam of the moisture originally contained in it, as well as the removal of all the substances which evaporate at the sterilisation temperature reached.

In accordance with a further characteristic of this invention the steam generated during the sterilisation heat treatment of the comminuted material is recovered, subjected to a further sterilisation at high pressure and condensed to be subsequently reincorporated into the sterilised comminuted material, with which it is delivered to the discharge.

Advantageously the condensed steam and sterilised comminuted material are intimately mixed and simultaneously cooled to obtain a paste which is subsequently subjected to compaction and briquetting and then discharged.

The advantages and the characteristics of this invention will become more apparent from the following description of an embodiment of a process for continuous sterilisation of hospital refuse, made from hereon with reference to the attached drawings by way of indication only.

Figure 1:
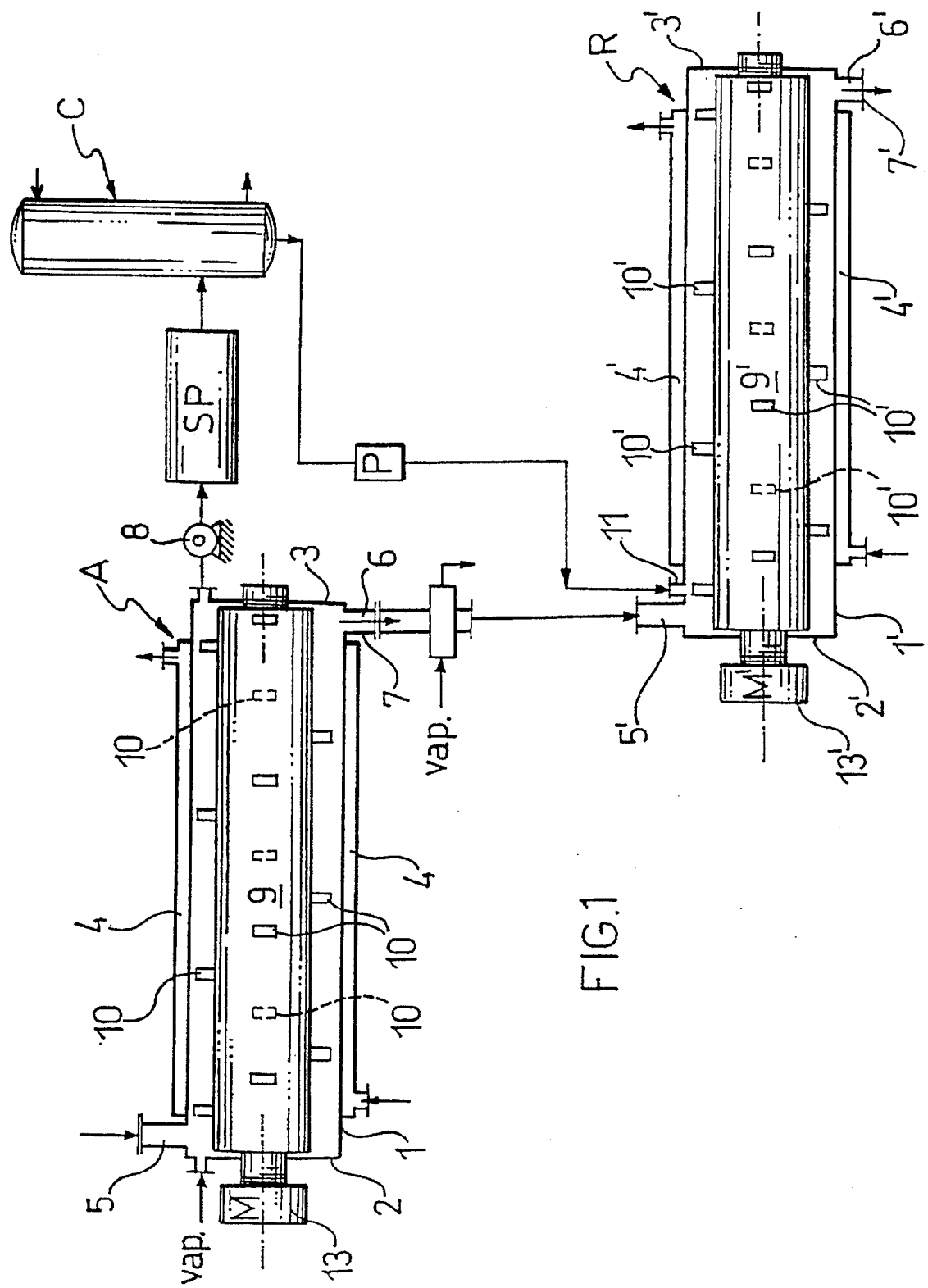
FIG. 1 is a schematic representation of apparatus for performing the process of the invention.

With reference to FIG. 1 the apparatus utilised for the process according to the invention for continuous sterilisation of hospital refuse comprises first apparatus A which hereinafter in the description will be called a turbosteriliser, second apparatus R hereinafter called a turbocooler, a high pressure steriliser SP and a condenser C.

The turbosteriliser A essentially comprises a cylindrical tubular body 1 preferably disposed with its axis horizontal, closed at its opposite ends 2,3 and provided coaxially with a heating jacket 4 intended to receive appropriate heating means, for example an electrical resistance, a diathermic fluid or oil, or the like.

The tubular body 1 is provided with an inlet aperture 5 for comminuted material obtained by finely comminuting hospital refuse, and a discharge aperture 6 for the treated comminuted material.

This aperture 6 is in communication via a duct 7 with the inlet aperture 5' of the turbocooler R.

Rotatably supported in the tubular body 1 is a paddle rotor 9. The paddle 10 of this rotor are disposed helically and are orientated to centrifuge the comminuted material against the internal wall of the tubular body itself and simultaneously to convey this material towards the discharge aperture 6. A motor 13 is provided to drive the paddle rotor at a speed variable from 400 to 1500 revolutions per minute.

The turbocooler R essentially comprises a cylindrical tubular body 1', preferably disposed with its axis horizontal, closed at its opposite ends 2'3' and provided with a coaxial cooling jacket 4' intended to be traversed, for example, by a refrigerant liquid.

The tubular body 1' is provided with an inlet opening 5' for the material treated in the turbosteriliser A and a cooled material discharge opening 6'.

A paddle rotor 9' is rotatably supported in the tubular body 1', the paddles 10' of which are disposed helically and are oriented to centrifuge and simultaneously convey the material subject to treatment towards the outlet.

A motor 13' is provided for driving the rotor 9' at a speed variable from 400 to 100 revolutions per minute.

The high pressure steriliser SP is of conventional type and is in communication with the turbosteriliser A via a suction-blower unit 8 and, on Eke opposite side, with the condenser C. This latter, which is of conventional type, is in turn in contact with the turbocooler R through a pump P.

Advantageously the delivery duct of the pump P is in communication with the interior of the turbocooler R via a liquid inlet aperture 11 provided close to the inlet opening 5' for the sterilised comminuted material coming from the turbosteriliser A.

Figure 2:
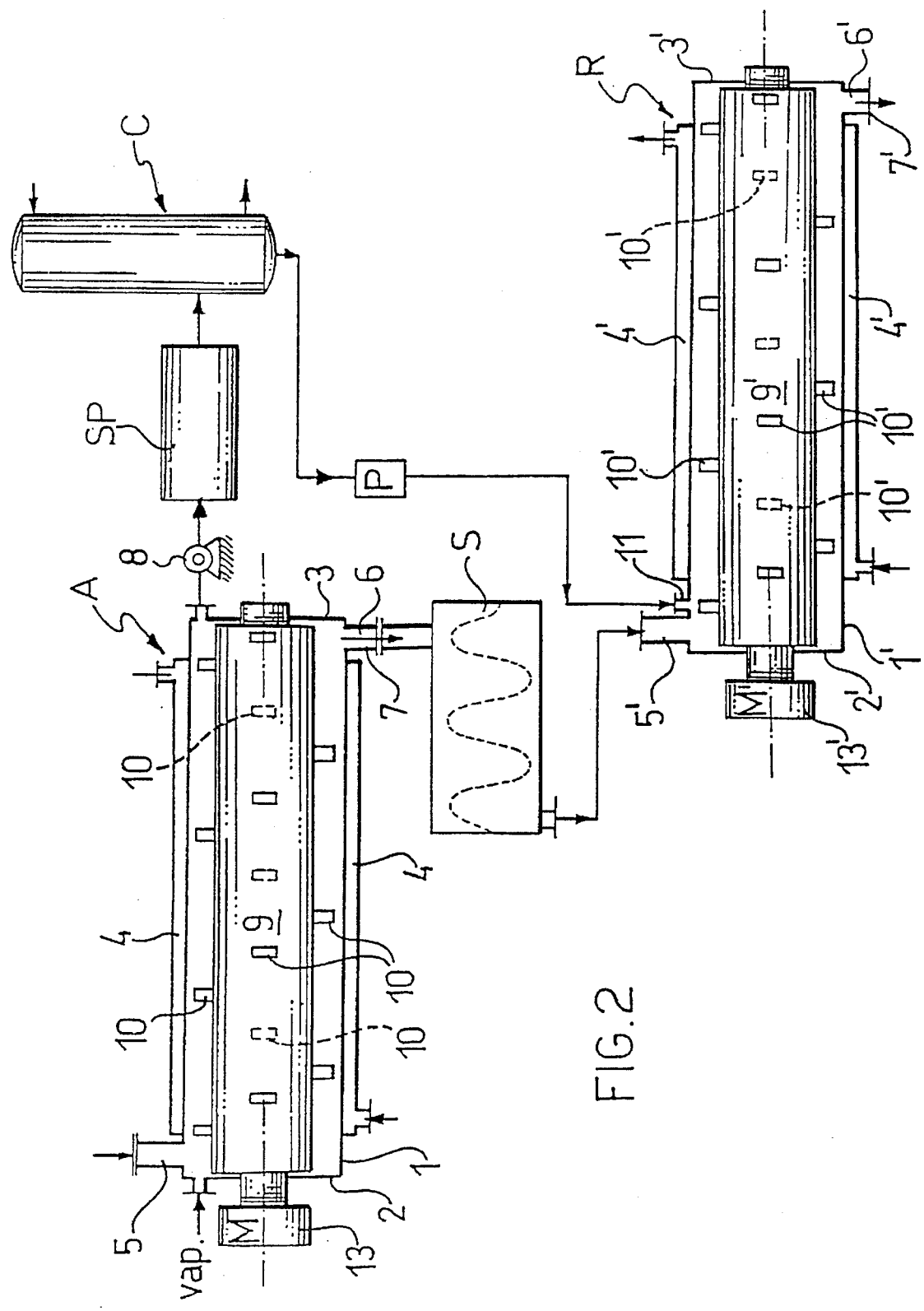
FIG. 2 is a schematic representation of the apparatus used to perform a variant in the said process.

With reference to FIG. 2, in which all the same components as those already described have the same reference numerals, the apparatus used in a variant of the method of the invention includes a stabiliser S maintained at a temperature lying between 100° and 300° C., which acts to determine the time for which the product leaving the turbosteriliser A remains at high temperature.

Figure 3:
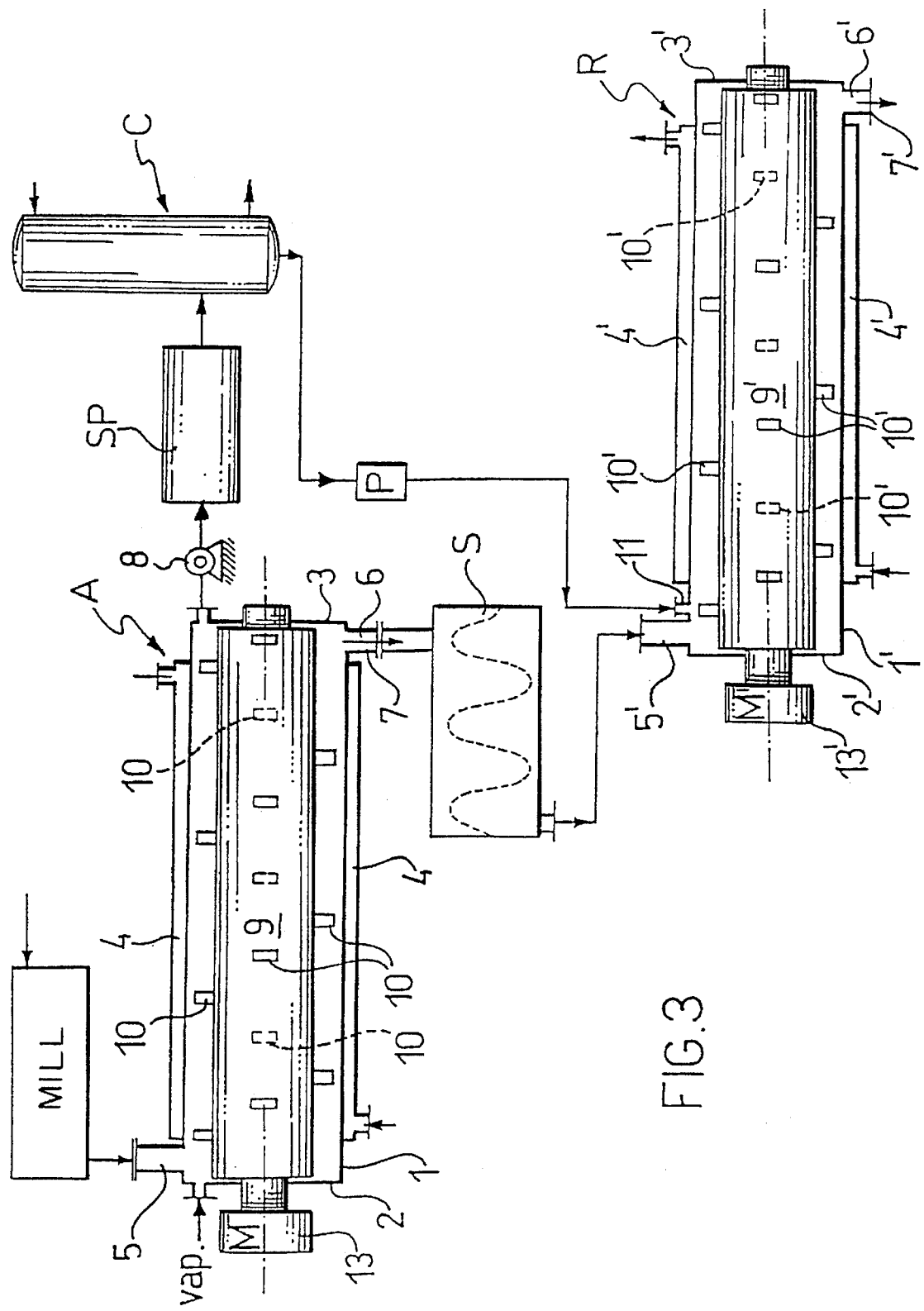
FIG. 3 schematically illustrates a complete installation for disposal of refuse containing pathogens, including the apparatus necessary for performing the process of the invention.

With reference to FIG. 3, the installation for disposal of pathogen-containing refuse comprises, in addition to the apparatus already illustrated in the preceding Figures, an indicated with the same reference numerals, a mill of conventional type, for example a multiple mill, the output product of which is continuously fed to the turbosteriliser A.

According to the method of this invention the hospital refuse is subjected wholly (that is to say all of the components of which it is composed) to a forced grinding in an appropriate mill until it reaches an appropriate grain size such that it can be pumped or conveyed in a screw conveyor; in general, and preferably, these components, after comminution, have an almost powder-like consistency, with a moisture content variable from 5 to 30% by weight.

A continuous flow of the various different comminuted components thus obtained is fed continuously, to the turbosteriliser A (through the inlet aperture 5 thereof) from the input of which it is taken and mechanically "worked" by the paddles of the rotor 9, which are maintained at an appropriate speed of rotation.

The speed of rotation of this paddle rotor 9 is chosen in such a way that from the inlet of the turbosteriliser A the comminuted material is centrifuged against the hot internal wall of the turbosteriliser itself and accelerated (with respect to the speed of flow at the inlet) towards the outlet so as to be "transformed" from a solid vein flow into a thin tubular layer dynamic in substantial contact with the hot wall of the turbosteriliser, dynamic in that it is continuously displaced towards the outlet opening; the comminuted material is maintained in a highly turbulent state within the thin tubular layer by the mechanical action of the paddles of the rotor.

It is thus apparent that all of the individual particles of comminuted material are indiscriminately brought into contact with the hot wall of the turbosteriliser for a very large but indefinite number of times, thereby undergoing a corresponding number of heat exchanges, just as corresponding heat exchanges are experienced by the remaining particles of the thin layer. Consequently the sterilisation heat treatment is guaranteed for each particle of this thin layer contrary to what occurs in the bulk treatment of hospital refuse in the prior art.

It has been established that wall temperatures of between 200° and 500° C., and preferably between 350° and 400° C., are more than sufficient for a total sterilisation of hospital refuse thus treated.

It is to be noted that simultaneously with the sterilization, drying of the (originally wet) comminuted material also takes place with the generation of steam; this steam is more than sufficient to render the material itself non-flammable, thereby eliminating any possible risk of fire.

To this end a flow of steam or inert gas can advantageously be introduced into the turbo sterilizer.

The vapours generated within the turbosteriliser, which include steam and substances which evaporate at the sterilisation temperature used, are recovered, for example sucked out from the turbodrier itself and subjected to a sterilisation at high pressure, preferably 10 to 12 atmospheres, and to condensation.

The sterilised and dry comminuted material at the output of the turbosteriliser can be sent, after cooling, to a conventional discharge.

In accordance with a further characteristic of the present invention this material is supplied to a turbocooler into which the condensed steam mentioned above is simultaneously supplied. In the turbocooler an intimate mixture between the condensate and the sterilised dry comminuted material takes place to obtain a paste which, at the output of the turbocooler, has a consistency and a temperature allowing it to be easily compacted and briquetted into the form of blocks. These blocks are subsequently discharged or sent to other destinations.

In a preferred embodiment of the invention the material at the output of the turbosteriliser is sent to a stabiliser S in which it is maintained at a temperature lying between 100° and 300° C. for a sufficient time, for example 2–10 minutes to guarantee the total elimination of sporogenic germs.

The stabiliser can be constituted by a static furnace with a timed discharge or, preferably, a low speed screw conveyor system.

The high pressure sterilisation can be replaced by other known sterilisation systems adapted for gases and vapours, such as, for example, those based on ultra violet rays.

In FIG. 3 is shown the arrangement of a complete installation for performing the method of the invention which includes a mill, usually of the multiple acting type able to comminute material of diverse consistency, such as, for example, plastics, rubber, cellulose, glass and steel and continuously to supply the turbosteriliser A described above. The installation is completed by a high pressure steriliser SP, a condenser C, a stabiliser S, a turbocooler R and apparatus, not shown, for compaction or briquetting of the product at the output of the turbocooler R.

EXAMPLE

By utilising the apparatus shown and described above, and following the method of the invention, the material coming from the hospital refuse comminution step in the form of a powder containing an average moisture of about 20% by weight, was continuously supplied into the turbosteriliser A at a flow rate of 300 kg per hour, in co-current with a flow of saturated steam.

The wall temperature was controlled about the value of 350° C., whilst the speed of rotation of the paddle rotor was maintained constantly at 850 revolutions per minute. After about three minutes the flow of steam was interrupted, whilst after a delay time of ten minutes dried comminuted material was discharged from the turbosteriliser. This material, having a moisture content of 1.5% by weight and a temperature of 130° C. was then fed continuously into the stabiliser S. The said material was maintained at a temperature of 150° C. for ten minutes before being discharged and fed continuously into the turbocooler R.

The vapours generated in the turbosteriliser, aspirated out from it were subjected to a pressure of twelve atmospheres in the high pressure steriliser SP and condensed in the condenser C.

The sterilised and stabilised comminuted material was then intimately mixed with the sterile liquid condensate coming from the condenser C in the turbocooler R.

The wall temperature in the turbocooler R was about 0° C., whilst the speed of rotation of the paddle rotor was maintained constantly at 650 revolutions per minute. After a delay of about ten minutes a paste was discharged from the turbocooler R which was subsequently sent to compression in the compactor.

A micro biological examination conducted on samples taken both from the output product from the turbocooler and the product output from the turbosteriliser, after incubation at 20° and at 37° respectively, both in aerobic and in anaerobic conditions, detected absolutely no development of microbic forms.

The invention thus conceived can be subject to variations and modifications, all lying within the ambit of protection thereof. It remaining understood that the critical fundamental condition of the method of this invention for the continuous sterilisation of hospital refuse is constituted by the heat treatment of this refuse reduced to comminuted material of appropriate grain size in a thin and dynamic layer, many variations can be introduced thereto even at the level of the composition of the comminuted material, such as the chemical/physical quantities in play, and the structural characteristics of the apparatus, all as a function of the particular and contingent requirements which it is intended to attribute to the final product, beyond those specifically aimed at by the present invention. Thus, for example, additives such as binding substances can be added for the purpose of modifying the characteristics of the final product.

I claim:

1. A method for disposal of hospital refuse and refuse including pathogenic components, comprises the steps:

comminuting said refuse to obtain a comminuted material which can be pumped;

feeding a continuous flow of said comminuted material to a turbosteriliser; said turbosteriliser having a cylindrical tubular body provided with a heating jacket and inlet and outlet apertures for material to be treated and treated material respectively, and a paddle rotor rotatably supported within the cylindrical body and driven to rotate at 400–1500 revolutions per minute, said cylindrical body having internal cylindrical walls heated to a temperature of 200° to 500° C.;

centrifuging said comminuted material to form a thin turbulent layer which is caused to flow continuously in contact with said heated walls towards said outlet aperture, thereby simultaneously sterilising said comminuted material; and cooling and recovering said sterilised comminuted material to produce sterilized comminuted material and subsequently delivering it to a discharge.

2. A process according to claim 1, further comprising a step of introducing a flow of saturated steam into said turbosteriliser concurrently with the continuous flow of comminuted material to be sterilised.

3. A process according to claim 2, further comprising a step of subjecting said sterilised comminuted material received from the outlet aperture of said turbosteriliser to heat sterilisation at 100° to 300° C. before sending said sterilised comminuted material to said cooling and recovery stage.

4. A process according to claim 3, further comprising a step of directing steam through said comminuted material during said centrifuging step, and simultaneously drying and sterilising said comminuted material.

5. A process according to claim 3, further comprising a step of aspirating said saturated steam from said turbosteriliser and subjecting said steam to sterilization at a pressure of 10 to 12 atmospheres and condensing said sterilised steam.

6. A process according to claim 5, further comprising a step of mixing said sterilized comminuted material at the outlet aperture of said turbosterilizer with said condensed steam to obtain a paste which is subsequently subjected to briquetting and then delivered to a discharge.

7. A process according to claim 6, wherein said mixing is performed in a turbocooler having a second cylindrical tubular body provided with a cooling jacket and an inlet opening for the sterilized comminuted material from said turbosterilizer, and said condensed steam, and a discharge opening for the paste formed therein, and a paddle rotor rotatably supported within the second cylindrical body and driven to rotate at between about 100 to 200 revolutions per minute.

8. A process according to claim 2, further comprising a step of directing steam through said comminuted material during said centrifuging step, and simultaneously drying and sterilising said comminuted material.

9. A process according to claim 2, further comprising a step of aspirating said saturated steam from said turbosteriliser and subjecting said steam to sterilization at a pressure of 10 to 12 atmospheres and condensing said sterilized steam.

10. A process according to claim 9, further comprising a step of mixing said sterilized comminuted material at the outlet aperture of said turbosterilizer with said condensed steam to obtain a paste which is subsequently subjected to briquetting and then delivered to a discharge.

11. A process according to claim 10, wherein said mixing is performed in a turbocooler having a second cylindrical tubular body provided with a cooling jacket and an inlet opening for the sterilized comminuted material from said turbosterilizer, and said condensed steam, and a discharge opening for the paste formed therein, and a paddle rotor rotatably supported within the second cylindrical body and driven to rotate at between about 100 to 200 revolutions per minute.

12. A process according to claim 1, further comprising a step of directing steam through said comminuted material during said centrifuging step, thereby simultaneously drying and sterilising said comminuted material.

13. A process according to claim 12, further comprising a step of aspirating said steam from said turbosteriliser and subjecting said steam to sterilization at a pressure of 10 to 12 atmospheres and condensing said sterilised steam.

14. A process according to claim 13, further comprising a step of mixing said sterilized comminuted material at the outlet aperture of said turbosterilizer with said condensed steam to obtain a paste which is subsequently subjected to briquetting and then delivered to a discharge.

15. A process according to claim 14, wherein said mixing is performed in a turbocooler having a second cylindrical tubular body provided with a cooling jacket and an inlet opening for the sterilized comminuted material from said turbosterilizer, and said condensed steam, and a discharge opening for the paste formed therein, and a paddle rotor rotatably supported within the second cylindrical body and driven to rotate at between about 100 to 200 revolutions per minute.

16. A method for disposal of hospital refuse and like refuse including pathogenic components, comprising the steps of comminuting said refuse to obtain a comminuted material which can be pumped;

feeding a continuous flow of said comminuted material to a turbosteriliser; said turbosteriliser having a cylindrical tubular body provided with a heating jacket and inlet and outlet apertures for material to be sterilised and sterilised material respectively, and a paddle rotor rotatably supported within said cylindrical body and driven to rotate at 400–1500 revolutions per minute, said cylindrical body having internal cylindrical walls heated to a temperature of 200° to 500° C.;

sterilising said comminuted material by centrifuging said comminuted material to form a thin turbulent layer which is caused to flow continuously in contact with said heated walls toward said outlet aperture;

drying said comminuted material during said sterilising step by introducing a flow of saturated steam into said turbosteriliser and directing said saturated steam through said comminuted material;

removing said steam from said turbosteriliser after said steam has been directed through said comminuted material, and subjecting said removed steam to sterilisation at a pressure of 10 to 12 atmospheres and condensation; and cooling and recovering said comminuted material and delivering said comminuted material to a discharge.

17. A method for disposal of hospital refuse and like refuse including pathogenic components, comprising the steps of comminuting said refuse to obtain a comminuted material which can be pumped;

feeding a continuous flow of said comminuted material to a turbosteriliser; said turbosteriliser having a cylindrical tubular body provided with a heating jacket and inlet and outlet apertures for material to be sterilised and sterilised material respectively, and a paddle rotor rotatably supported within said cylindrical body and driven to rotate at 400–1500 revolutions per minute, said cylindrical body having internal cylindrical walls heated to a temperature of 200° to 500° C.;

sterilising said comminuted material by centrifuging said comminuted material to form a thin turbulent layer which is caused to flow continuously in contact with said heated walls toward said outlet aperture;

drying said comminuted material during said sterilising step by introducing a flow of steam into said turbosteriliser and directing said steam through said comminuted material;

removing said saturated steam from said turbosteriliser after said steam has been directed through said comminuted material, and subjecting said removed steam to sterilisation at a pressure of 10 to 12 atmospheres and condensation;

receiving said comminuted material from said outlet aperture of said turbosteriliser and further sterilising said comminuted material by subjecting said comminuted material to heat at 100° to 300° C.; and mixing said sterilised and dried comminuted material with said sterilised and condensed steam to obtain a paste which is subsequently subjected to briquetting, and delivering said paste for discharge; said mixing being performed in a turbocooler which includes a second cylindrical tubular body provided with a cooling jacket, a first inlet opening for receiving said sterilised and dried comminuted material from said outlet aperture of said turbosteriliser, a second inlet opening for receiving said sterilised and condensed steam, and a discharge opening for said paste, and a second paddle rotor rotatably supported within said second cylindrical body and driven to rotate at between about 100°–200° revolutions per minute.

* * * * *